US012745938B2

United States Patent
(12) United States Patent
Dech et al.

(10) Patent No.: US 12,745,938 B2
(45) Date of Patent: Sep. 29, 2026

(54) FETAL MAGNETOCARDIOGRAPHY SYSTEMS AND METHODS

(71) Applicant: CloudNav Inc., San Jose, CA (US)

(72) Inventors: Jeffery Dech, San Jose, CA (US); Erik E. Anderson, Mountain View, CA (US); Ben Kokes, San Mateo, CA (US)

(73) Assignee: CloudNav Inc., San Jose, CA (US)

(*) Notice: Subject to any disclaimer, the term of this patent is extended or adjusted under 35 U.S.C. 154(b) by 0 days.

(21) Appl. No.: 18/596,975

(22) Filed: Mar. 6, 2024

(65) Prior Publication Data

US 2024/0298950 A1 Sep. 12, 2024

Related U.S. Application Data

(60) Provisional application No. 63/489,039, filed on Mar. 8, 2023.

(51) Int. Cl.
*A61B 5/243* (2021.01)
*A61B 5/00* (2006.01)

(52) U.S. Cl.
CPC ............ *A61B 5/243* (2021.01); *A61B 5/6804* (2013.01); *A61B 5/721* (2013.01); *A61B 5/7221* (2013.01);

(Continued)

(58) Field of Classification Search
CPC ....... A61B 5/243; A61B 5/6804; A61B 5/721; A61B 5/7221; A61B 5/726;

(Continued)

(56) References Cited

U.S. PATENT DOCUMENTS 8,731,646 B2 * 5/2014 Halperin .................. A61B 5/11
600/509
2004/0034299 A1 * 2/2004 Kandori ................. A61B 5/243
600/409

(Continued)

OTHER PUBLICATIONS

Hamelm,Ann, Paul, "Doppler ultrasound technology for fetal heart rate monitoring: a review", IEEE transactions on ultrasonics, ferroelectrics, and frequency control 67.2, 2019, 226-238, 13 pages.

(Continued)

*Primary Examiner* — Baisakhi Roy
(74) *Attorney, Agent, or Firm* — Ashurst Perkins Coie US LLP

(57) ABSTRACT

Devices, systems and methods for monitoring of fetal health through determination of fetal heart rate are described. In an example, beat-to-beat decelerations and accelerations are monitored to estimate fetal position and orientation within the womb using magnetometer sensors. The described embodiments enable long-term monitoring that can be remote from a clinical setting, and is sufficiently portable to be operable while the mother engages in substantial motion during daily activity. An example method includes receiving, from a magnetic sensor, a combined heart signal comprising a mixture of a maternal heart signal and the fetal heart signal, estimating, based on the combined heart signal, one or more parameters associated with a location/motion of the magnetic sensor, generating a de-noised combined heart signal by performing a de-noising operation on the combined heart signal, and tracking, based on the de-noised combined heart signal, an estimate of the fetal heart signal.

21 Claims, 11 Drawing Sheets

(52) U.S. Cl.
CPC .......... *A61B 5/726* (2013.01); *A61B 2503/02* (2013.01); *A61B 2562/0219* (2013.01); *A61B 2562/0223* (2013.01)

(58) Field of Classification Search
CPC ........ A61B 2503/02; A61B 2562/0219; A61B 2562/0223; A61B 5/02411
See application file for complete search history.

(56) References Cited

U.S. PATENT DOCUMENTS

| | | | | |
|---|---|---|---|---|
| 2005/0165323 | A1* | 7/2005 | Montgomery | A61B 5/369 128/903 |
| 2018/0110434 | A1* | 4/2018 | Lau | A61B 5/02427 |
| 2018/0317783 | A1* | 11/2018 | Petrikovsky | A61B 5/02411 |
| 2019/0320944 | A1* | 10/2019 | Vaidyanathan | A61B 5/7264 |
| 2020/0072916 | A1* | 3/2020 | Alford | G01R 33/0017 |
| 2020/0107771 | A1* | 4/2020 | Penders | A61B 5/6833 |
| 2021/0386315 | A1* | 12/2021 | Anderson | A61M 25/0127 |
| 2022/0330885 | A1* | 10/2022 | Xu | A61B 8/488 |
| 2023/0218219 | A1* | 7/2023 | Keenan | A61B 5/7221 600/511 |
| 2023/0329944 | A1* | 10/2023 | Erasala | A61B 5/242 |
| 2024/0206842 | A1* | 6/2024 | Vajinepalli | A61B 8/5269 |

OTHER PUBLICATIONS

Ramli, Dzatia. , "Blind source separation (BSS) of mixed maternal and fetal electrocardiogram (ECG) signal: A comparative study.", Procedia Computer Science 176 (2020): 582-591, 10 pages.

Strand, Sarah, "Low-cost fetal magnetocardiography: a comparison of superconducting quantum interference device and optically pumped magnetometers.", Journal of the American Heart Association 8.16: e013436, 2019.

Orang Alem et al: "Fetal magnetocardiography measurements with an array of microfabricated optically pumped magnetometers" Physics in Medicine and Biology, Institute of Physics Publishing, Bristol GB, vol. 60, No. 12, Jun. 4, 2015 (Jun. 4, 2015), pp. 4797-4811, XP020286626, ISSN: 0031-9155, DOI: 10. 1088/0031-9155/60/12/4797 [retrieved on Jun. 4, 2015] * Abstract, Introduction, pp. 4798-4801, 4803, 4805, 4807, 4808; figures 4, 6, 7, 8, 15 pages.

Barbara Grimm: "Recommended Standards for Fetal Magnetocardiography", PACE—Pacing and Clinical Electrophysiology., vol. 26, No. 11, Nov. 1, 2003 (Nov. 1, 2003), pp. 2121-2126, XP0093158113, us ISSN: 0147-8389, DOI: 10.1046/j.1460-9592.2003.00330.x * p. 2123, paragraph 8, 6 pages.

EP: extended European Search Report dated May 17, 2024 for Application No. 24 162 055.8, 12 pages.

EP: Office Action dated Jun. 3, 2025 for Application No. 24 162 055.8, 9 pages.

Schmidt A et al., "Developing fetal motor-cardiovascular coordination analyzed from multi-channel magnetocardiography", Physiological Measure, Instittue of Physics Publishing Bristo, GB, vol. 35, No. 10, Sep. 17, 2014, pp. 1943-1959, XP020271410, ISSN: 0967-3334, DOI: 10.1088/0967-3334/35/10/1943.

* cited by examiner

FETAL MAGNETOCARDIOGRAPHY SYSTEMS AND METHODS

CROSS-REFERENCE TO RELATED APPLICATION

This patent document claims priority to and benefits of U.S. Provisional Patent Application No. 63/489,039, filed on Mar. 8, 2023. The entire content of the before-mentioned patent application is incorporated by reference as part of the disclosure of this patent document.

TECHNICAL FIELD

This document generally relates to magnetocardiography, and more particularly, to estimating maternal and fetal heart signals using magnetic sensors.

BACKGROUND

In general, the fetal heart rate can be measured by various technologies, which can be categorized into technologies for intermittent and continuous fetal heart rate measurements. They have different clinical objectives: intermittent measurement techniques are used for verification of fetal life or assessment of cardiac performance, whereas continuous measurement techniques allow obstetricians to obtain detailed physiological information about newborns.

SUMMARY

Embodiments of the disclosed technology relate to methods, systems, and devices for fetal magnetocardiography (fMCG). The disclosed embodiments advantageously enable long-term monitoring that can be remote from a clinical setting, and are sufficiently portable so that they can operate while the mother engages in substantial motion during daily activity. In an example, this is achieved using magnetic sensors that can operate in a magnetically unshielded environment and do not require cryogenic cooling.

In an example aspect, a system for monitoring a fetal heart signal in a subject includes at least one magnetic sensor configured to measure a combined heart signal comprising a mixture of a maternal heart signal and the fetal heart signal. In an example, the at least one magnetic sensor is configured to operate within a dynamic range from 0.01 pT to 1 mT and with a noise floor within a range from 0.01 pT/$\sqrt{\text{Hz}}$ to 100 pT/$\sqrt{\text{Hz}}$. The system further includes a processor configured to receive, from the at least one magnetic sensor, the combined heart signal. The processor is then configured to estimate, based on the combined heart signal, one or more parameters associated with a location or a motion of the at least one magnetic sensor, and generate a de-noised combined heart signal by performing a de-noising operation on the combined heart signal. In an example, the de-noising operation comprises a filtering operation configured based on the one or more parameters. Finally, the processor is configured to track, based on the de-noised combined heart signal, an estimate of the fetal heart signal.

In another example aspect, a method for monitoring a fetal heart signal in a subject includes receiving, from at least one magnetic sensor, the combined heart signal, and estimating, based on the combined heart signal, parameters associated with a location or a motion of the at least one magnetic sensor. The method further includes configuring, based on the parameters, a denoising operation, generating a denoised combined heart signal by performing the denoising operation on the combined heart signal, and tracking, based on the de-noised combined heart signal, an estimate of the fetal heart signal.

In yet another example aspect, a method for estimating a fetal heart position includes loading model constraints and initial parameter estimates, localizing sensors relative to beacon locations, generating sensor locations in body coordinates, and solving an inverse magnetic model for the fetal heart position.

In yet another example aspect, the above-described method may be implemented by an apparatus or device that includes a processor and/or memory.

In yet another example aspect, this method may be embodied in the form of processor-executable instructions and stored on a computer-readable program medium.

The subject matter described in this patent document can be implemented in specific ways that provide one or more of the following features.

DETAILED DESCRIPTION

Figure 1A:
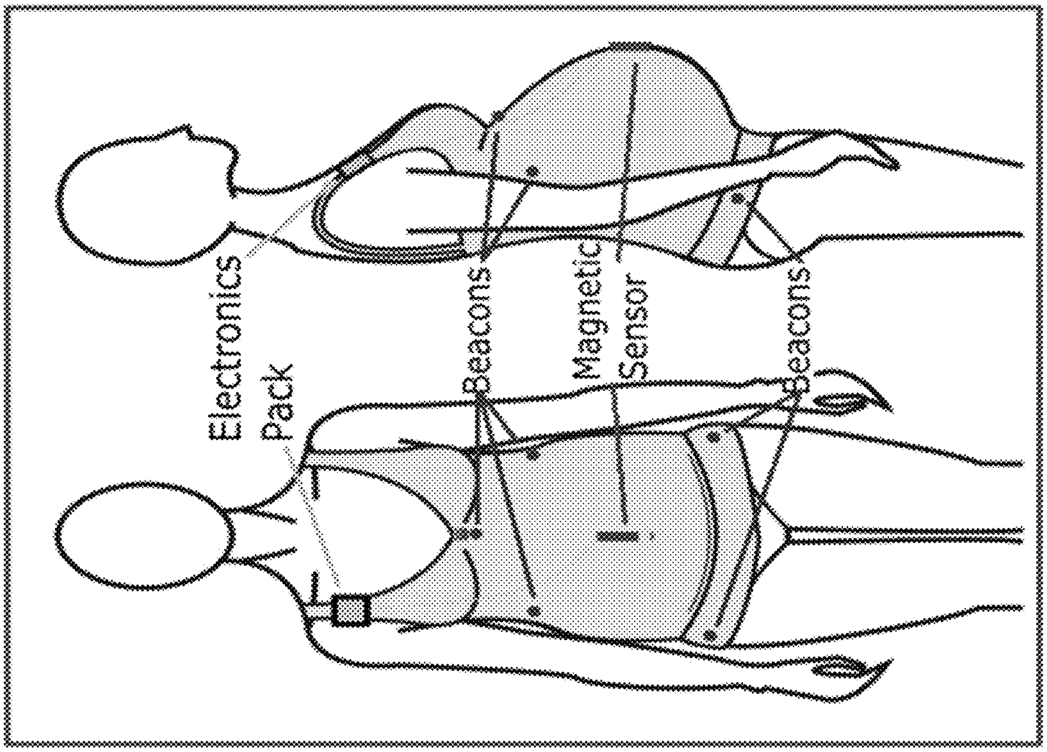
FIGS. 1A and 1B illustrate example systems for fetal magnetocardiography with a single magnetometer and multiple magnetometers, respectively.

Devices, systems, and methods for determining and monitoring a fetal heart rate signal are described. Section headings are used in the present document to improve readability of the description and do not in any way limit the discussion or the embodiments (and/or implementations) to the respective sections only.

Overview of Fetal Heart Rate Signal Monitoring

Monitoring fetal heart signals is extremely important for evaluating fetal well-being during pregnancy and labor. Fetal heart rate variability has been shown to be a very important marker of health and is often monitored throughout labor. Measuring the characteristics of individual heart beats is also of clinical value. Tracking fetal movement throughout the day is also a common metric used by doctors to assess health and could be done using heart signals if one could associate them with the heart's orientation. Various modalities have previously been used to monitor fetal heart signals.

During the 19th century, fetal heart rate measurement was performed by stethoscope, which was later improved to an optimized fetal stethoscope. A large improvement in signal quality was achieved in 1960 using fetal scalp electrodes connected during labor, and after the mother's membranes had ruptured. Given the very high SNR achieved, the fetal scalp electrode has remained the gold standard for measuring the comparison performance of other modalities of fetal heart monitoring. However, this method is extremely invasive and can only be used after membranes have been ruptured.

In the 1960s and 1970s, ultrasound Doppler measurements (e.g., as described in U.S. Pat. No. 4,143,650) offered a far less invasive method for identifying and tracking fetal heart rate prior to and during labor, quickly becoming the standard method. While still quite useful in a clinical setting, this method requires significant training to perform correctly and suffers from several drawbacks. For example, it is extremely sensitive to motion artifacts, resulting in a low accuracy of individual R-R pulse intervals (i.e., R-wave peak to R-wave peak, which represents the measurement of the sinus heart period in chronological or heartbeat order). Therefore, data is typically averaged over a 15-second interval. Identifying fetal distress relies significantly upon being able to correctly identify short term deceleration and acceleration of the fetal heart rate, a requirement that is not adequately met by Doppler ultrasound measurements. This makes acquisition take longer and does not represent true real-time tracking. Even under trained clinician control, Doppler ultrasound has a much higher rate of heart rate confusion (identifying maternal heart rate by mistake instead of the fetal heart rate) than more recent modalities.

The next big jump in monitoring capability relied on the use of ECG electrodes to measure potential on the mother's abdomen near the fetus, and on advances in signal processing to separate the stronger maternal heart signal and isolate the fetal heart signal. Multi-electrode systems (e.g., as described in GB 2482758) were first used in clinical settings to monitor mothers shortly before and during labor. These systems provide much better estimates of fetal heart rate, including legitimate single beat timing measurements, such as R-R interval times. The ECG systems also have a much lower confusion rate than the Doppler ultrasound methodology. Further advances in these systems have made them cable-less, allowing mothers to move, shower, and walk while typically using a double belt system to hold the ECG electrodes and communication module. Although these systems represent a big step forward in both measurement performance and comfort for the mother, there are still some difficulties and drawbacks with these systems. In particular, the ECG electrodes must continuously maintain firm contact with the mother's skin. For example, it can be difficult to keep the electrodes adequately attached, especially if the mother moves significantly, there is typically some amount of irritation and redness at the electrode site after a monitoring session, and there are also some distortions in the electrode potential measurements due to the varying dielectric properties of body tissue between the fetal heart and the external electrodes. Furthermore, ECG signals are also significantly attenuated during the vernix period, which occurs after the 27th week of pregnancy. During this period, the ECG signals experience added attenuation from the *vernix* caseosa, a biofilm covering the fetus which acts as a dielectric.

The ECG modality for identifying and tracking fetal heart rate has recently started moving out of clinical environments and is being pilot tested for remote monitoring under physician care (e.g., as described in U.S. Pat. No. 10,039,459 and US 2021/0259613) in rural areas where it is challenging for mother to access a clinical monitoring site. Other modalities include ultra-wideband (UWB) radar detection (e.g., as described in U.S. Pat. No. 9,078,582) to measure fetal heart rate and its variability.

An alternative to ECG systems are systems that measure fetal heart signals magnetically, termed magnetocardiography (MCG). There are several benefits to MCG over ECG. For example, the magnetic system does not require positive electrode contact with the skin, and magnetic measurements of fetal heart signals are also significantly less distorted by body tissues and are less affected by motion artifacts than ECG measurements.

Fetal MCG systems have previously used SQUID (superconducting quantum interference device) magnetometers (e.g., as described in U.S. Pat. No. 8,374,672) and optically pumped magnetometers (OPMs) in controlled laboratory and specific clinical environments. Both these types of sensors suffer from a very small dynamic range (~55 nT) which requires them to be operated in a magnetically shielded room. SQUID sensors also require cryogenic cooling with liquid helium or liquid nitrogen while OPMs require precision laser systems to operate.

Therefore, both systems require a footprint which restricts their portability.

2 Example Embodiments of the Disclosed Technology

The described embodiments benefit from the measurement quality benefits of MCG over ECG, while overcoming the need for restrictive measurement conditions like cryogenic cooling or magnetic shielding. It achieves this by using a different type of magnetic sensor based on effects such as tunneling magnetoresistance (TMR), giant spin resonance (GSR), magneto-impedance (MI) or fluxgate magnetometry. Sensors based on these technologies can measure extremely weak magnetic signals over a much broader dynamic range than SQUID or OPM sensors. Using these high dynamic range sensors advantageously enables additional performance improvements over the ECG modality while enabling the system to be operated in unshielded spaces, including as a wearable device that can operate while the mother engages in significant motion and other everyday activities. The wearable device also represents another step forward in comfort due to the removal of the need for direct skin contact of the sensors, as is required in the ECG modality.

Figure 1B:
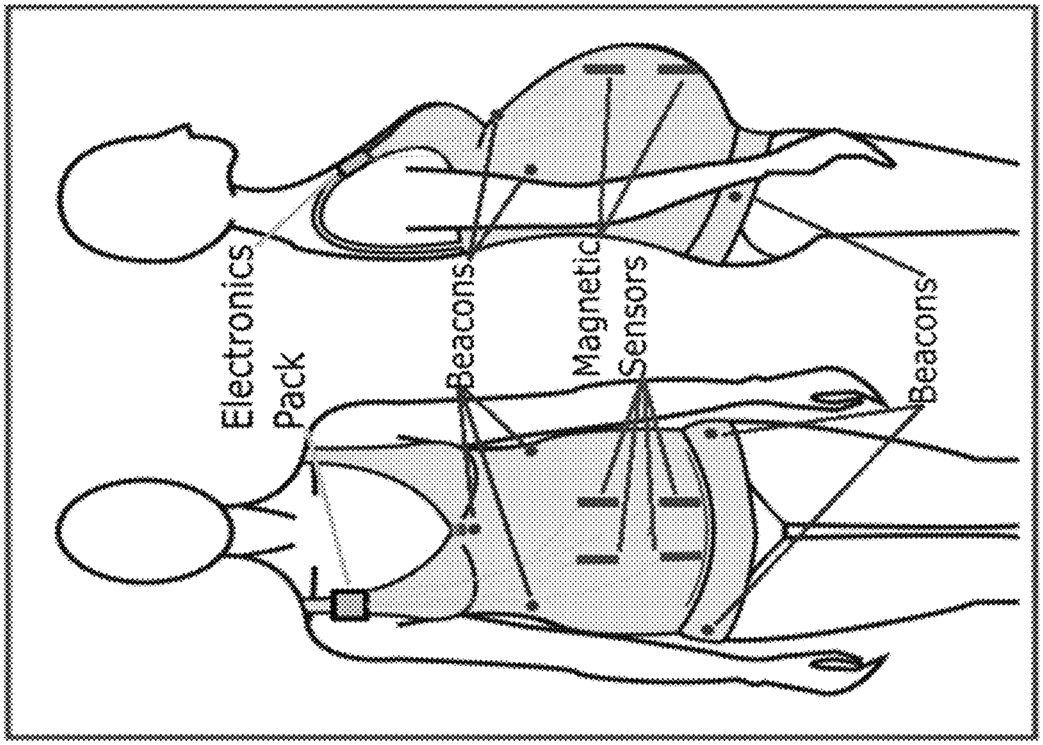

FIGS. 1A and 1B illustrate example systems for fetal magnetocardiography (fMCG), in accordance with the disclosed technology. As shown in FIGS. 1A and 1B, the fMCG system can use a single magnetometer or multiple magnetometers, respectively, that communicates with a sensor (or electronics) pack, and further includes multiple beacons that are used to provide a reference frame. Communication between the magnetometers and the electronics pack, and the beacons and the electronics pack, can be wired (e.g., as shown for the magnetometers in FIGS. 1A and 1B) or wireless (e.g., using a wireless protocol like Bluetooth, Bluetooth Low Energy, Zigbee, Wi-Fi, and the like).

In some embodiments, the systems shown in FIGS. 1A and 1B are implemented without beacons, and alternative techniques are used to establish a reference frame, as described in this patent document.

Figure 2:
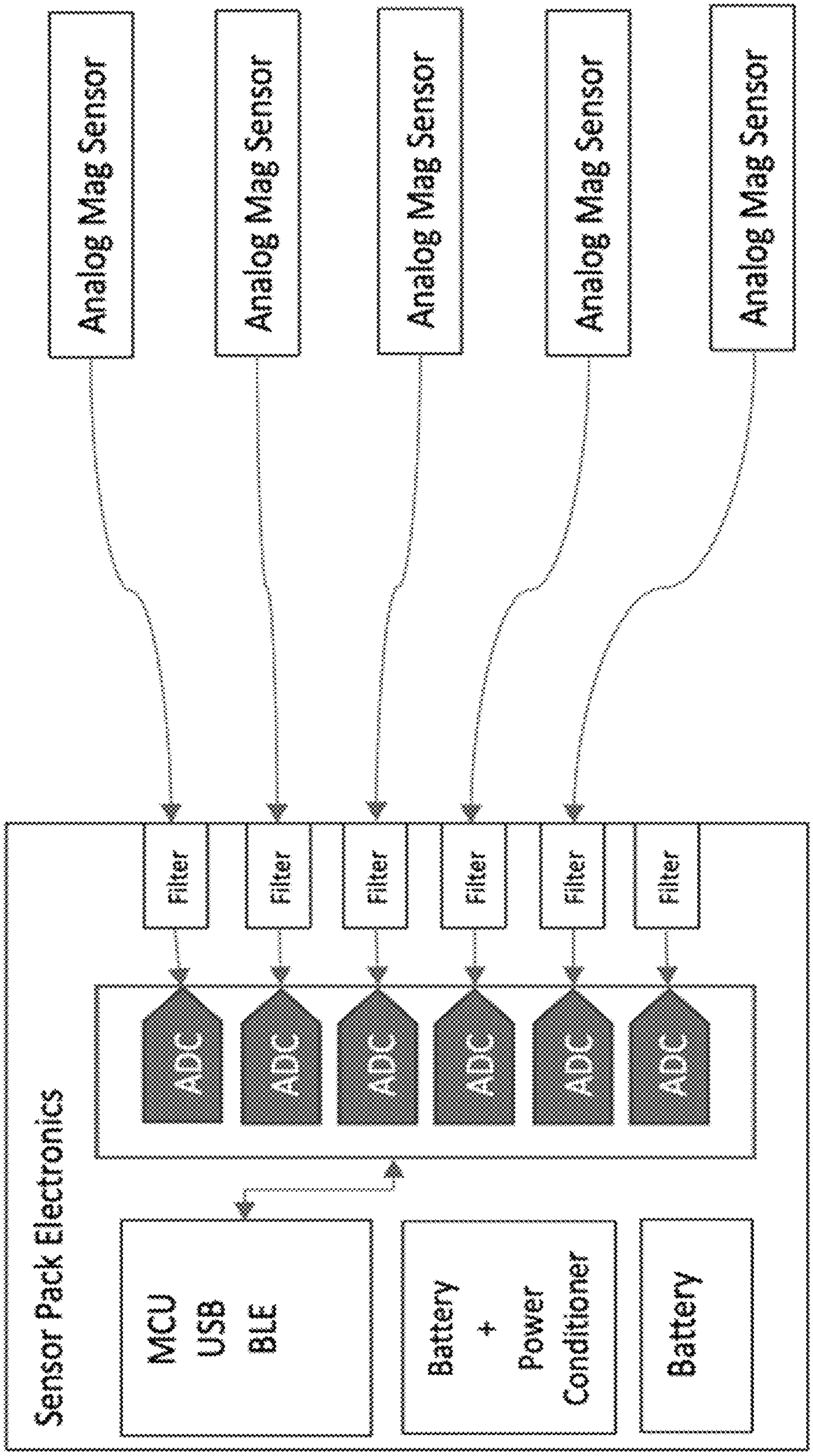
FIG. 2 is a block diagram illustrating the components of example electronics that communicate with multiple magnetometers.

FIG. 2 is a block diagram illustrating the components of an example electronics pack that communicates with multiple magnetometers. As shown therein, the electronics pack includes one or more power sources (e.g., the battery, and the battery and power conditioner), a microcontroller unit (MCU), a USB connector, and a Bluetooth Low Energy (BLE) transceiver. The electronics pack includes a multiple filters, each of which is used to filter an incoming signal that is received, via a lead, from a corresponding magnetometer. The received analog signal from a particular magnetometer is filtered using, for example, a filter that implements bandpass and notch filtering, to pre-condition the signal before digital sampling. The particular magnetometer signal is then sampled using a respective analog-to-digital converter (ADC). The digital filtered signal is then sent to the MCU via, for example, a serial peripheral interface (SPI) or an inter-integrated circuit (I2C). In some embodiments, a smaller processor marshals the data from the ADCs before transmission to the processor. In the embodiment shown in FIG. 2, the electronics pack includes a dedicated ADC and filter for each magnetometer in the fMCG system. This advantageously ensures that the signals from multiple magnetometers can be processed in parallel, providing near real-time monitoring of the fetal and maternal heart rate signals. Alternatively, the electronics pack could be configured to use a single filter and ADC to process the received signals sequentially if power consumption or footprint of the circuitry were greater concerns during routine remote monitoring.

2.1 Magnetometers (or Magnetic Sensors)

Existing systems employ SQUID and OPM sensors, which require magnetically shielded rooms and/or either specialized cooling or electronics systems to operate. Embodiments of the disclosed technology uses magnetic sensors that can operate outside of a magnetically shielded room, since they have a much larger dynamic range, and require no cryogenic cooling. Sensors of this type include those based on tunneling magnetoresistance (TMR), giant spin resonance (GSR), and fluxgate magnetometers.

In some embodiments, a magnetometer used in an example fMCG system has the following properties:

operation within a wide dynamic range spanning 0.01 pT to 1 mT;

operation with a noise floor in the 0.01 pT/$\sqrt{\text{Hz}}$ to 100 pT/$\sqrt{\text{Hz}}$ range;

operation in a magnetically unshielded environment;

operation without cryogenic cooling; and operation with a frequency response in a range spanning 0.1 Hz to 200 Hz.

2.2 Separation of Heart Signals

Due to the proximity to both the maternal and fetal hearts, the magnetometer sensors will typically measure some linear combination of the maternal and fetal heart signals, as well as noise. The amount of signal energy from each source will be determined by the sensor's physical proximity to each of the hearts. The described embodiments apply signal processing techniques to separate the maternal and fetal heart rate signals before each of them are processed further.

Figure 3:
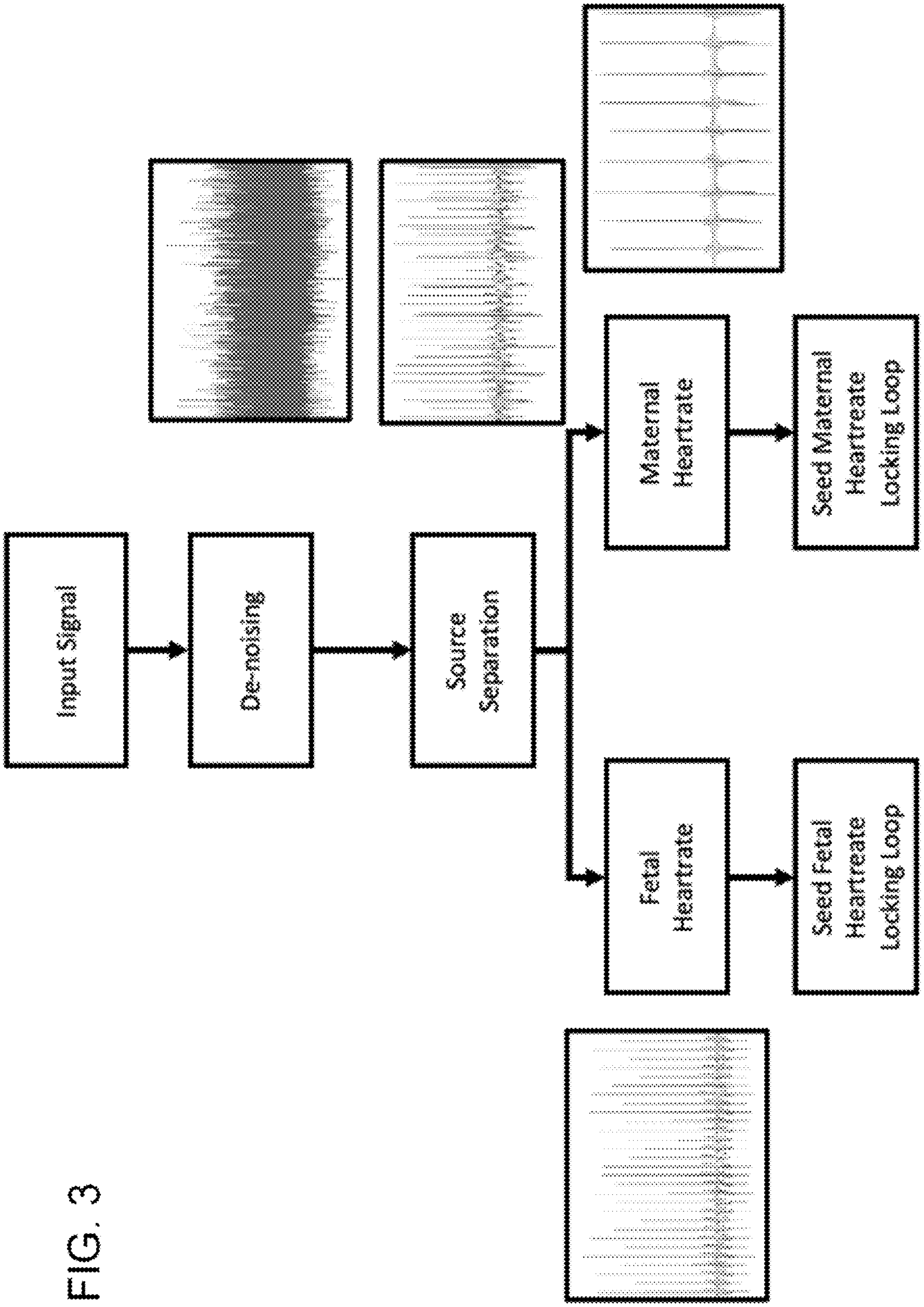
FIG. 3 is a flow diagram illustrating an example method for separating maternal and fetal heart rate signals from a received magnetometer signal.

FIG. 3 is a flow diagram illustrating an example method for separating maternal and fetal heart rate signals from a received magnetometer signal. As shown therein, the process starts with a de-noising operation (as described in Section 2.2.1) followed by a source separation operation (as described in Section 2.2.2). Once the maternal and fetal heart rate signals have been separated, the signals can be used to seed a lock in loop to track the fetal and maternal heartbeats (as described in Section 2.2.3) individually.

2.2.1 De-Noising

In some embodiments, the de-noising operation applies bandpass filtering to the time-domain signal. For example, the band between 0.1 Hz-50 Hz may be filtered (using a bandpass filter), and an additional notch filtering operation at 60 Hz (50 Hz in parts of the world) and its harmonics (120 Hz, 180 Hz, etc.) may be applied (using a notch filter) to eliminate noise from the AC wall power. In other embodiments, the bandpass and notch filtering operations may be implemented using wavelet analysis or machine learning techniques, e.g., neural networks.

Motion artifacts. When the mother moves, small changes in the local magnetic field will be observed by the sensors which represent undesirable signals. These changes are termed motion artifacts. The position estimation parameters are used as an input to an adaptive filter which attenuates the motion artifacts, ideally eliminating them.

In some embodiments, the de-noising operation incorporates the position or motion information of the magnetometers and/or subject to filter motion artifacts from the magnetometer signals. In an example, motion information is obtained using an inertial measurement unit (IMU). The IMU obtains data using internal gyroscopes, accelerometers and possibly magnetometers. Motion parameters such as position, velocity and acceleration are estimated from the IMU. The rotational and linear motion parameters can be extracted using techniques such as sensor fusion (e.g., as described in U.S. Pat. No. 10,989,563, which is incorporated, in its entirety, as part of this document). Herein, motion parameters in three-dimensional space may be represented using a quaternion algebra or a combination of Cartesian co-ordinates and Euler angles.

The magnetometer output is fixed to the static reference frame (e.g., as detailed in Section 2.3) using the motion parameters and short-term changes in them. As the mother moves, the magnetic sensors move and rotate as a consequence. The direction in which magnetic signals are observed to point can change, even if the total magnitude and position in space remain constant. These rotational changes are tracked through the motion parameters, allowing the measurements to be related back to the static reference frame established by the system using a simple rotational transform.

In some embodiments, motion artifacts can also be tracked using a "trust mask" which is a metric used by the system to indicate the confidence it has that the magnetic signals observed at some instant in time originate from an actual magnetic source rather than being motion induced. This trust mask can be used for downstream processing, de-weighting data taken during intervals of strong motion.

2.2.2 Source Separation

In some embodiments, source separation techniques are applied to either the output of an individual sensor or a plurality of sensors at once to isolate the maternal and fetal heart signals from the measured superposition signals. In an example, independent component analysis (ICA) or principal component analysis (PCA) may be used to implement source separation. These techniques use a plurality of sensor inputs to separate the signals using a statistical metric. Other methods rely on the input from only a single sensor. For example, neural network (machine learning) approaches, can be used to separate out multiple sources from time-domain signals, rendering them as independent signals.

2.2.3 Heartbeat Tracking

The human heart rate is variable within the population and the heart rate of mother and fetus are at very different rates. Even for an individual, the heart rate can vary over several minutes due to a variety of normal and abnormal physiological factors. Embodiments of the disclosed technology estimate the heart rate, as well as monitor them over time to track changes therein. Since the maternal heart beats at 60-90 beats per minute (bpm) while the average fetal heart beats at 120-160 bpm, the signals have energy at different frequency bands. Therefore, once the signals have been identified, the described embodiments use a locked loop to identify the fetal and maternal heart beats separately based on their unique cadences.

In some embodiments, the maternal and fetal heartrates are monitored using an initial acquisition and tracking loop model. In an example, the heart rates are obtained sequentially, first tracking the mother or fetus' heart rate before the other. In another example, the two heartrates are tracked in parallel tracking loops or simultaneously within the same loop.

In the acquisition stage, the heart rate is acquired, estimating it from the magnetometer when the heart rate is still unknown. By measuring the magnetic signals over some interval of time, the system makes a statistical estimate of the observed heartrate's parameters, such as its frequency and phase (e.g., what time index corresponds to the R-peak or some other marker). Once this estimate is achieved with a statistical confidence above some threshold, the heart rate is considered acquired. The trust mask obtained from the position data can be used to statically de-weight magnetometer data obtained during periods of motion.

A tracking loop is then initiated after acquisition. Starting with the parameter estimates from the acquisition phase, an adaptive method updates them using incoming heart beats, adjusting them as they change. In some embodiments, a Kalman filter may be employed to update the parameters during the tracking loop.

The heart rate parameters can be used to identify time intervals over which the individual heartbeats are expected to be observed in the magnetic data. These individual beats can be time sliced using this information. The heart rate parameters themselves can also be used by the system to improve monitoring and/or medical diagnosis.

2.3 Reference Frames

In some embodiments, known, nearly static reference points can be used to allow the system to relate the coordinate system of the device, to the coordinates of the mother's body and possibly to coordinates in a visual feedback system to the user. Any movement of the subject or the fetus can then be detected relative to this static reference frame.

In some embodiments, alternating current (AC) coils, referred to as "beacons", can be incorporated into the system, either embedded in a garment or the environment around the subject, as reference locations. The coils are controlled in such a manner that their signals can be unambiguously detected by the magnetic sensors. In an example, the coils can be operated simultaneously, whereas in another example, they are operated sequentially. In both examples, the coils can be unambiguously identified with that reference location by the system.

In some embodiments, the coils may be operated at independent frequencies, making the signal from each coil distinguishable from all others. In other embodiments, the coils may emit a spread spectrum signal, with each coil emitting a unique identifier such as a pseudo-random number, like in GPS. Alternatively, the coils may be operated simultaneously at the same frequency, which treats the coils as spatially distributed. In some embodiments, the reference coils are operated during the entire measurement, whereas in other embodiments, they are operated only some of the time.

In some embodiments, the maternal heart signal can be used in much the same manner as a beacon source. It can be assumed to be in a fixed position relative to the fetal heart rate signal and even relative to any shifting of the beacons or sensors. Therefore, it acts as a marker relating the garment co-ordinates to the physical co-ordinates of the mother's body.

Figure 4:
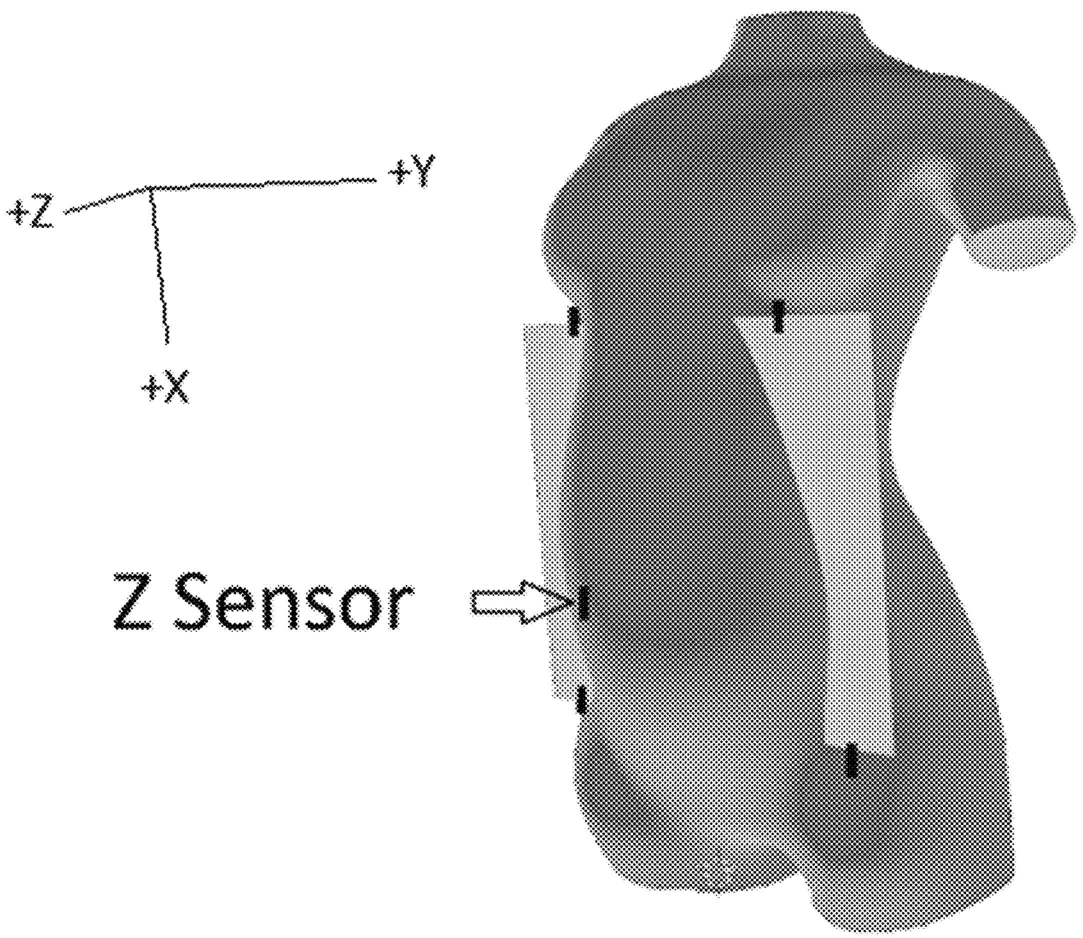
FIG. 4 illustrates an example of a reference frame.

In some embodiments, and as illustrated in FIG. 4, a set of five reference beacons can be used to create the frame. Four of the coils placed at the edges of the abdomen will be approximately co-planar. An xy-plane minimizing the total distance between the four points and the plane can be formed. Then, two mutually perpendicular vectors which lie in this plane are selected to form the x and y axes. A fifth coil placed near the navel can be used to measure the z-axis perpendicular to the fitted xy-plane.

2.4 User Adjustment and Feedback

Figure 5:
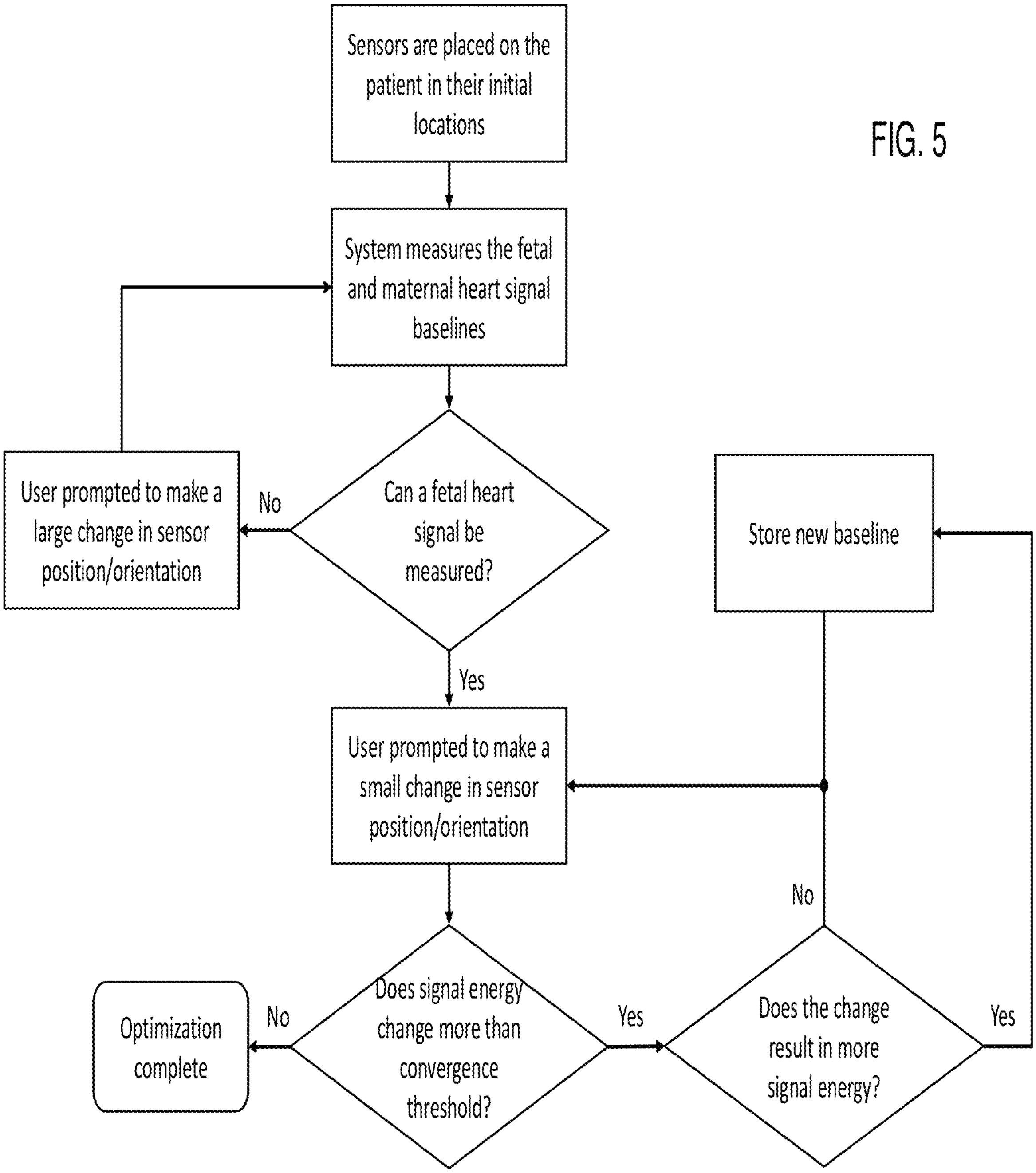
FIG. 5 is a flow diagram illustrating an example method for the optimal placement of magnetometers on a subject.

Embodiments of the disclosed technology are configured to use a reference frame, which provides a clear and effective way to transmit guidance to the user on how to adjust the position of the sensors, as illustrated in FIG. 5. As shown therein, the user is prompted to move the sensors relative to the reference frame and the change in signal energy is tracked. If the signal energy increases, the point moved to is kept as a baseline from which further moves are compared. If not, the original baseline position is used.

Figure 6:
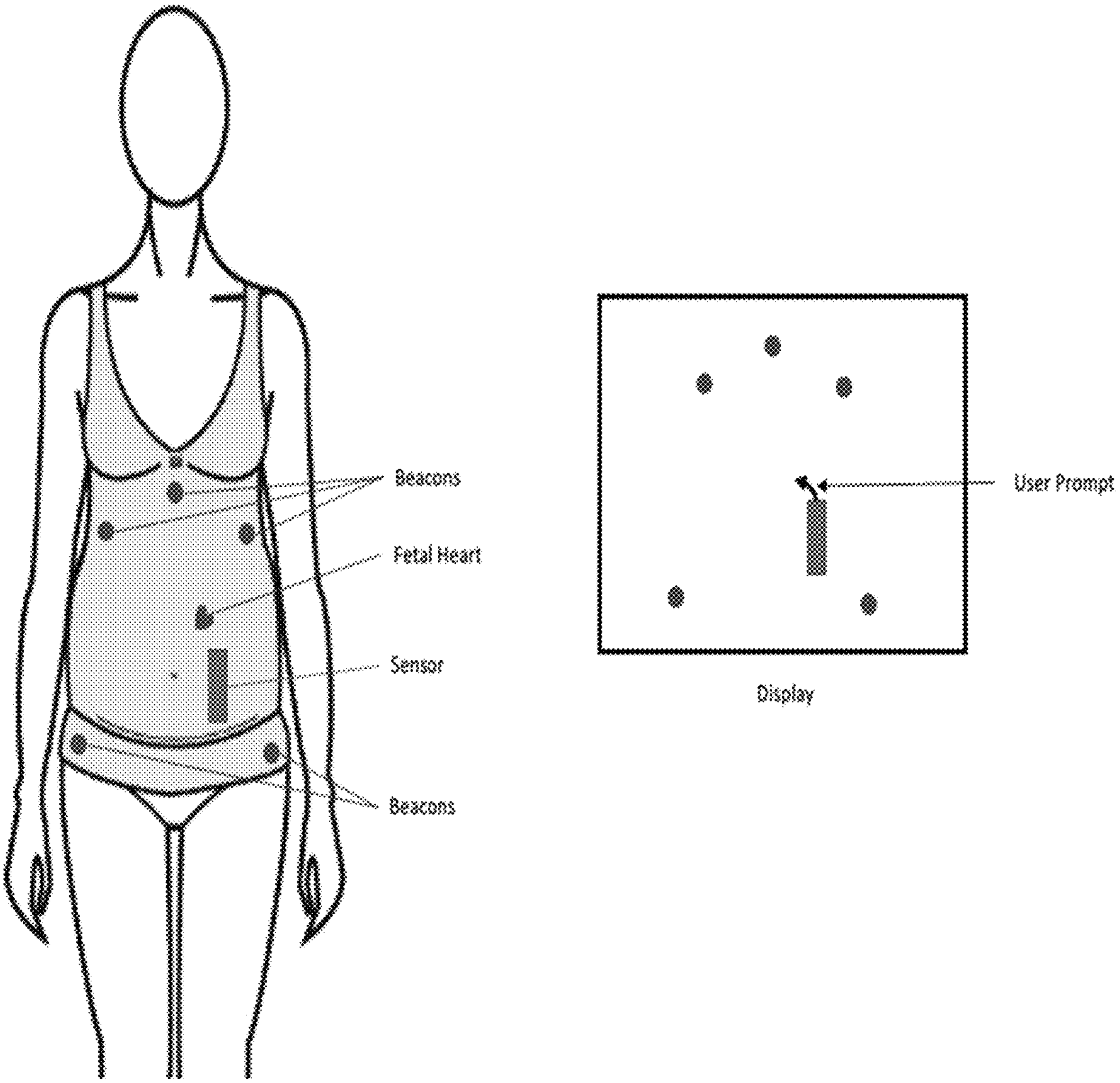
FIG. 6 illustrates an example of user feedback for positioning magnetometers.

FIG. 6 illustrates an example of a deployed fMCG system that is communicatively coupled to a graphical user interface (GUI) that displays the reference frame coordinates, as well as an arrow showing the direction the user is prompted to move the sensor. Cues that the sensor position is near optimal or that the sensor has lost track of the fetal or maternal heart signatures can also be displayed.

2.5 Fetal Tracking

Figure 7:
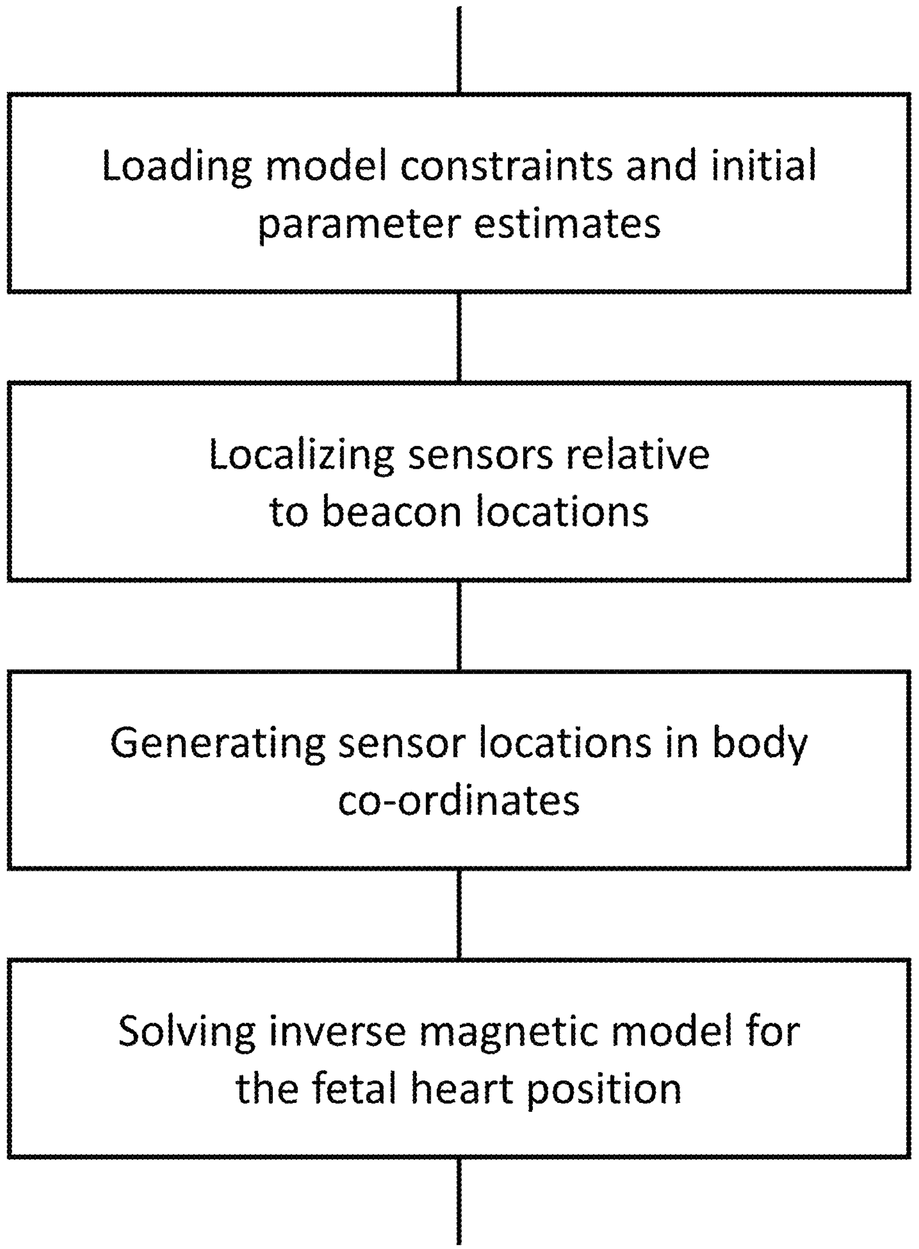
FIG. 7 is a flow diagram illustrating an example method for determining sensor locations and maternal and fetal dipole locations on a subject.

Embodiments of the disclosed technology are configured to track the position of the fetal heart. If the locations of the sensors are first determined, the position and strength of the fetal heart magnetic source distribution are determined using an inverse method. An example process flow is illustrated in FIG. 7. As shown therein, the locations of the sensors in the reference frame of the mother's body are estimated relative to each other and the reference frame of the mother's body. In some embodiments, this is achieved using a set of reference beacons emitting known signals. Inverse modeling of the sensor locations can be performed to estimate their positions. With the sensors localized, the position and strength of the fetal heart signal can then be determined.

2.5.1 Sensor Localization

In an example, a sensor's location relative to a sensor beacon of known strength whose magnetic field is approximated as a magnetic dipole source meaning that the field a position r from the dipole obeys the equation $$B(\vec{r}) = \frac{\mu_o}{4\pi}\frac{3\hat{r}(\vec{m}\cdot\hat{r}) - \vec{m}}{r^3}.$$

The location of the sensor $\vec{r}$ can be found using the inverse of the above equation.

In some embodiments, a total of five measurements are required. The location of the sensor and the dipole strength vector can be described by the parameter set (x, y, z, θ, ϕ, m) where x, y, and z describe the location of the sensor relative to the dipole in Cartesian co-ordinates, θ and ϕ describe the angular orientation of the dipole relative to the sensor and m is the dipole strength. As the dipole strength m is already known, there are five remaining unknown parameters to be solved. In embodiments where a three-axis magnetic sensor is used, the five measurements require the use of two sensors, since three measurements, in x, y, and z, are taken by the sensor for each beacon.

Figure 8:
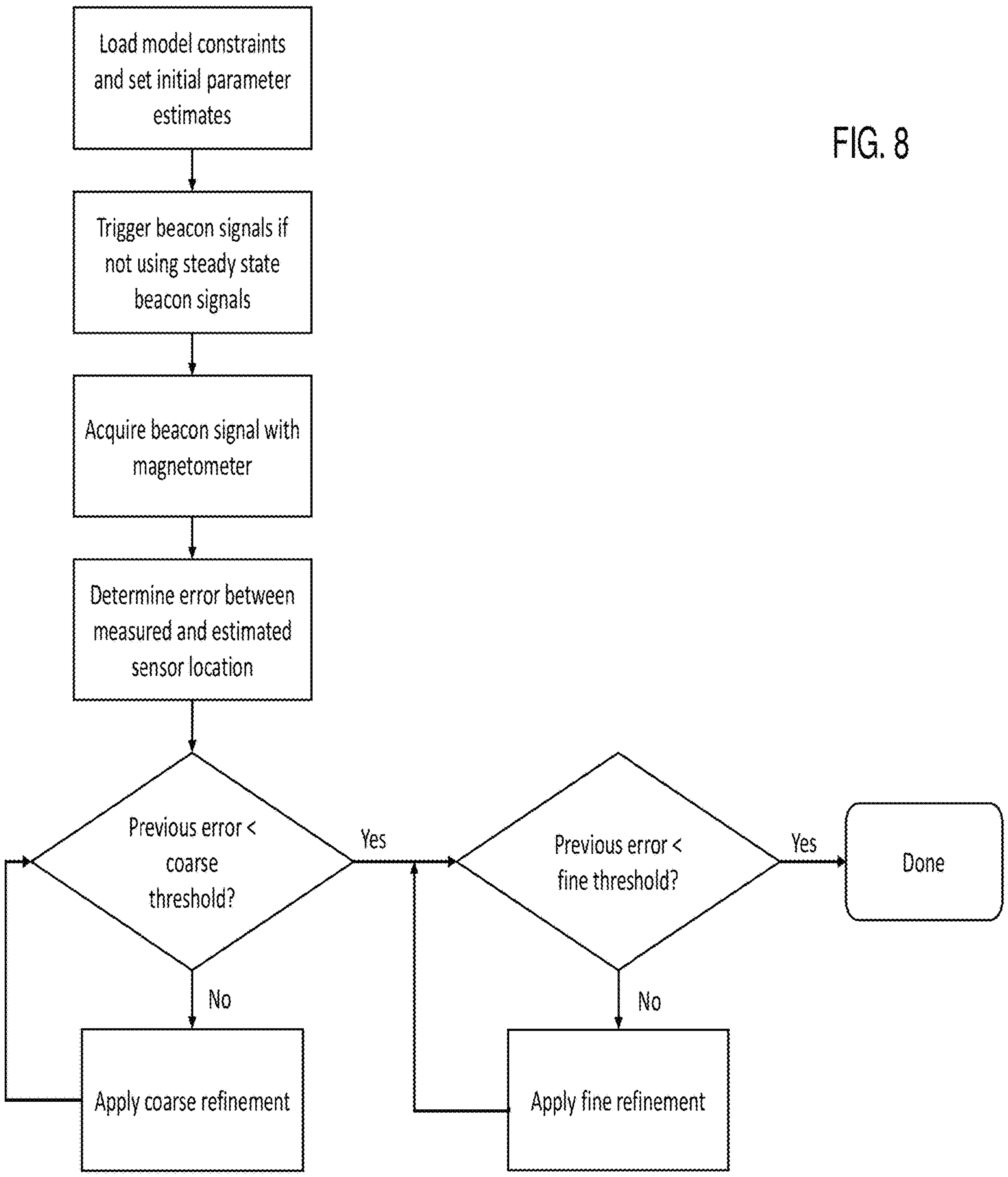
FIG. 8 is a flowchart of an example method for determining the sensor locations relative to a set of reference beacons.

In some embodiments, an iterative method can be used to solve the inverse problem, as illustrated in FIG. 8. As shown therein, the method starts by loading known constraints on the solution and an initial guess. The reference beacons are then triggered to emit a magnetic signal, if not already operating in a steady state mode. The magnetic sensors then acquire signals from each reference beacon either simultaneously or in serial, as required by the specific embodiment, and apply any required signal processing to determine the magnetic field strength of the signal from each beacon. At each iteration, the error between the measured magnetic field and the expected strength using the sensor's presumed location is computed. This error is used as the convergence metric for the solution.

Herein, the gradient of the error is used to update the parameter values. The derivative with respect to each parameter is calculated. The parameters are updated by the negative gradient times some proportionality constant (known as the learning rate). Some embodiments can separate the search into a coarse and fine grain method. The difference between the two steps being the magnitude of the learning during each iteration. The coarse stage will use a larger learning rate than the fine stage. If the error is below a coarse grain threshold, the coarse update is skipped. Iteration at the fine update size continues until a second, smaller fine grain threshold is reached at which point, the iterations stop.

2.5.2 Fetal Heart Inverse Modeling

The heart can be approximated as a magnetic dipole source following the formula given in Section 2.5.1. Using the readings from multiple sensors, the inverse of this equation can be solved to find the location of the dipole relative to the sensors and any beacons in the system.

In some embodiments, at least two measurements along each of the x, y, and z axes are required, for a total of six measurements. With at least six measurements, the location of the dipole in 3D space, the dipole strength, and the orientation of the dipole can be computed. Here, the orientation refers to the $\theta$ and $\phi$ angles in a spherical co-ordinate system. Each dipole is then described by the parameter set $(x, y, z, \theta, \phi, m)$ where m is the magnitude of the dipole.

In other embodiments, only five measurements are required by not measuring the $\theta$ angle, since a dipole source's field is symmetric in $\theta$. Here, the relative orientation of the dipole to the sensors can still be measured. However, ignoring the $\theta$ coordinate comes at the cost of being able to measure the relative distance to other dipole sources, e.g., the maternal heart signal.

Figure 9:
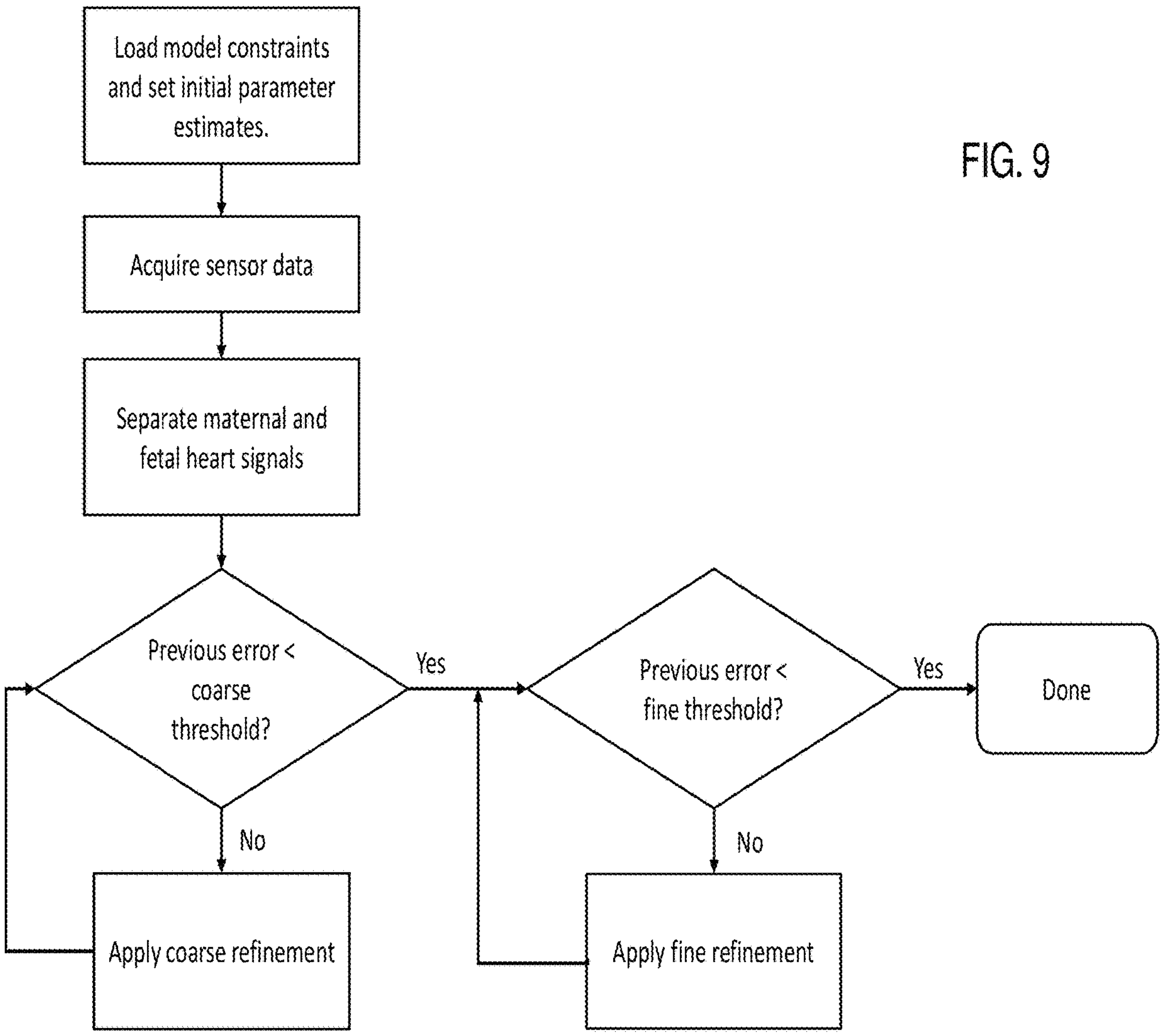
FIG. 9 is a flowchart of an example method for determining the magnetic dipole parameters of the fetal and maternal dipoles on a subject.

In some embodiments, the dipole location can be solved by an iterative method, as illustrated in FIG. 9. As shown therein, the method starts by loading an initial guess and physical constraints on the parameters. For example, constraining the distance between the maternal and fetal hearts to be within a certain range or limiting the magnitude of the fetal heart dipole to be within those known to be physically possible based on medical literature. At each iteration, the error between the expected measurements calculated from the parameter estimates and those observed with the actual sensors is computed. This is used as the convergence metric.

Herein, the gradient of the error is used to update the parameter values. The derivative with respect to each parameter is calculated. The parameters are updated by the negative gradient times some proportionality constant (known as the learning rate). Some embodiments can separate the search into a coarse and fine grain method. The difference between the two steps being the magnitude of the learning during each iteration. The coarse stage will use a larger learning rate than the fine stage. If the error is below a coarse grain threshold, the coarse update is skipped. Iteration at the fine update size continues until a second, smaller fine grain threshold is reached at which point, the iterations stop.

3 Example Methods and Implementations of the Disclosed Technology

Figure 10:
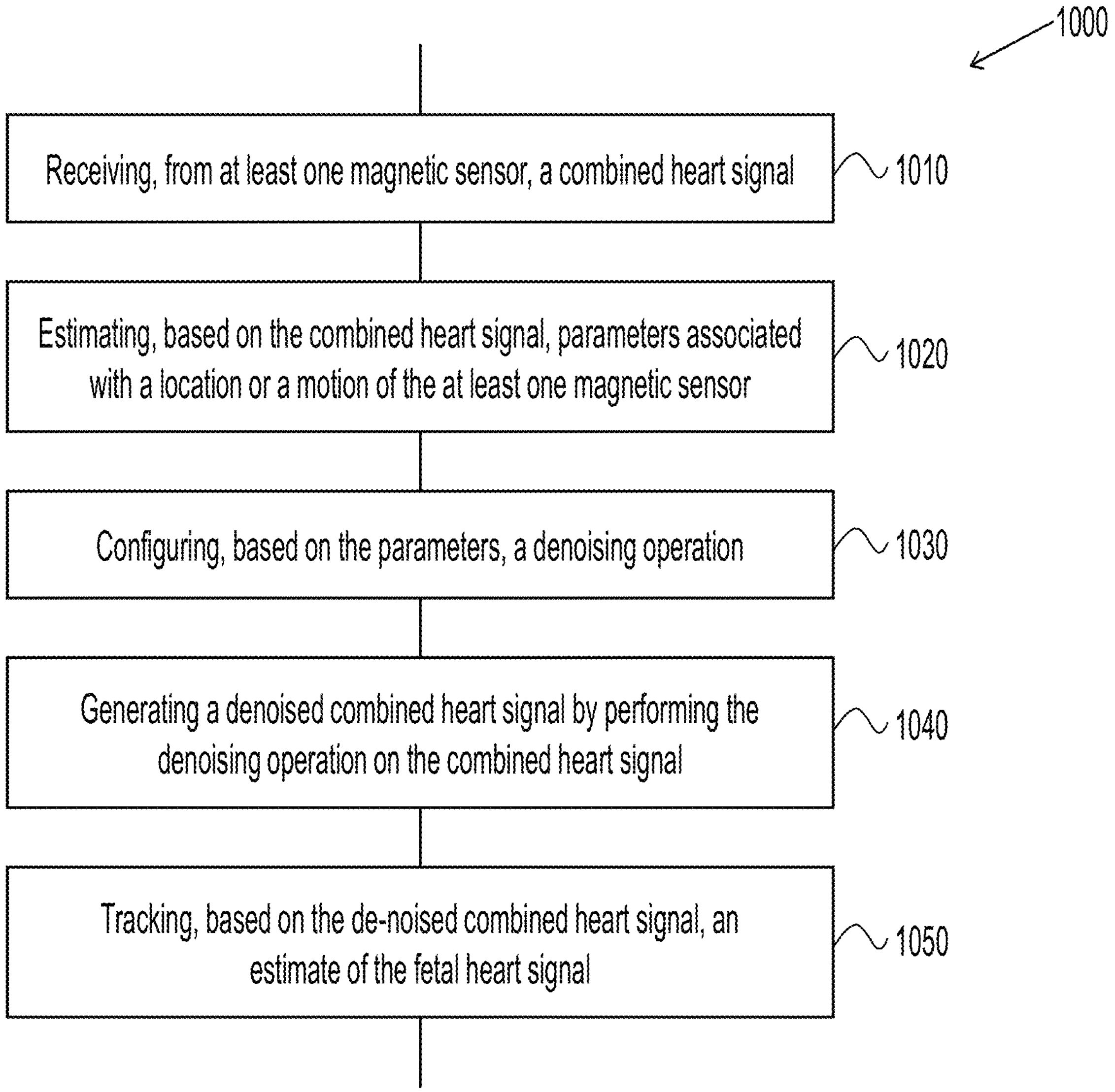
FIG. 10 is a flowchart of an example method for monitoring a fetal heart rate signal.

FIG. 10 shows a flowchart of an example method for determining and monitoring a fetal heart rate signal. The method 1000 includes, at operation 1010, receiving, from at least one magnetic sensor, the combined heart signal. In some embodiments, the combined heart signal is received through leads attached to the magnetic sensors and the electronics pack, e.g., as shown in FIGS. 1A and 1B that show fMCG systems that use a single and multiple magnetometers, respectively.

The method 1000 includes, at operation 1020, estimating, based on the combined heart signal, parameters associated with a location or a motion of the at least one magnetic sensor, and at operation 1030, the method 1000 includes configuring, based on the parameters, a de-noising operation. Determining location and/or motion parameters and performing de-noising is detailed in Section 2.2.1.

The method 1000 includes, at operation 1040, generating a denoised combined heart signal by performing the denoising operation on the combined heart signal.

The method 1000 includes, at operation 1050, tracking, based on the de-noised combined heart signal, an estimate of the fetal heart signal.

In some embodiments, the fetal heart rate signal can be isolated by performing a source separation operation on the denoised combined heart signal to generate an estimate of the maternal heart signal and an estimate of the fetal heart signal. The source separation operation, which may be implemented using ICA or PCA on signals from single or multiple sensors, is detailed in Section 2.2.3. Alternatively, the fetal heart rate signal is tracked in the denoised combined heart signal using a tracking loop and without explicitly separating the maternal and fetal heart rate signals.

The described embodiments provide the following systems, methods, and devices directed to fetal magnetocardiography:

1. A system for monitoring fetal heart signals using magnetometers
   a. Including data collection of a plurality of magnetic measurements, including computation means for detecting fetal heart signal from the magnetic measurements, isolating fetal heart signal from maternal heart signal, and extracting metrics on the fetal heart signal to indicate fetal health state and changes in fetal health stage.
   b. An example embodiment employs magnetic sensors which
      i. Operate within a wide dynamic range of 0.01 pT-1 mT
      ii. Have noise floors in the 0.01-100 $pT/\sqrt{Hz}$ range
      iii. Are capable of operating in a magnetically unshielded environment
      iv. Do not require cryogenic cooling
      v. Have operational frequency responses in the desired 0.1-200 Hz operating range c. Contains one or a plurality of magnetic sensors
i. An example embodiment is a single magnetometer embodiment using either a single axis or three axis magnetic sensor (e.g., as shown in FIG. 1A)
ii. In another, multiple magnetometers are used (e.g., as shown in FIG. 1B). Such a configuration can employ single axis sensors, three axis sensors or a plurality of both
d. The device has sensors in fixed, stable positions
i. The positions may be static or adjustable
ii. An example embodiment is a garment containing magnetic sensors mounted at stable positions (e.g., as shown in FIGS. 1A and 1B)
1. The sensor mount points may be adjustable by the user or through automated motorized control
2. The circuits, wires and sensors may be integrated into the garment
a. An example embodiment contains a single sensor placed near the center of the abdomen (e.g., as shown in FIG. 1A)
b. In another example, the garment has four sensors placed equidistant from the center of the abdomen (e.g., as shown in FIG. 1B)
c. In yet another example, the garment has multiple sensors that are placed about the center of the abdomen
iii. Another example is a self-standing unit, having sensors affixed to it, e.g., the sensors described in 1(b).
1. In an example embodiment, the unit with fixed sensors is positioned close to the mother
2. Another example has an operator or user position the sensors once the unit is close to the patient
3. In another example, the device uses motor control to position the sensors
iv. In another example, the magnetic sensors are connected to leads which are fixed to the patient using a temporary adhesive
v. In yet another example, the magnetic sensors are placed on one or more bands which are placed around the mother's abdomen 2. An example device for fetal MCG contains a readout circuit, power supply, power management, battery, a processor, and communications. This example device may include one or more of the components shown in FIG. 2. Alternatively, the embodiment shown in FIG. 2 may be augmented with the implemented described herein.
a. The communication may be wired or wireless
i. This may include communication to an application running on a user device such as a personal computer, tablet, or smart phone
b. The device may be embodied with a display (e.g., as shown in FIG. 6)

3. A method that identifies, separates, and tracks maternal and fetal heart signals from the time-domain input of the magnetic sensors (e.g., as shown in FIG. 3)
a. De-noising operations (e.g., described in Section 2.2.1) can be applied to the signal before separation
b. Source separation techniques (e.g., described in Section 2.2.2) are applied to separate the fetal and maternal heart signals
i. In an example embodiment, Independent Component Analysis (ICA) is used as the source separation technique
ii. In another example, Principal Component Analysis (PCA) is used
iii. In yet another example, wavelet analysis is used for source separation
iv. In yet another example, any combination of ICA, PCA, and wavelet analysis can be used to implement source separation.
c. Separated signals are used to form a locked tracking loop for continued separation
d. In some embodiments, the fetal and maternal heart signals are tracked using a tracking loop without explicitly separating the signals from the time-domain input of the magnetic sensors (but after denoising)
e. The described tracking loops are implemented using an initial acquisition operation and a subsequently tracking operation 4. A method to provide feedback on the estimated magnetic sensor locations. The feedback:
a. May be transmitted as visual feedback for devices embodied with a display (e.g., as shown in FIG. 6)
b. Can be used to reposition the sensors for improved signal quality
i. It determines when insufficient signal is present and provides feedback to the user on how to adjust the sensor locations for improved signal quality
ii. Monitors signals before and after adjustment to provide additional feedback to the user on where to move the sensors for improved position updates until the sensor position has sufficiently converged to the optimal point
c. May be fused with other datasets to provide feedback on optimal sensor locations
i. In an example embodiment, historical recordings are used as a baseline for expected signal levels, feedback is provided to the user to adjust the sensor until the signal converges to an acceptable ratio of the previously recorded signal energy
ii. In another, example datasets of known, good signals are stored in the device's memory and are compared to the acquired signals. Feedback is generated to guide the user to repositions the sensors until the signal converges to an acceptable ratio of the reference signal energy 5. A method that uses the stationary location of the maternal heart signal as a fixed reference coordinate system/framework
a. Can be used to locate the sensor and fetal heart positions relative to the coordinates of the maternal heart signal
b. Any other reference positions employed can be referenced relative to the maternal heart coordinates, e.g., beacons as shown in FIGS. 1A, 1B and 4

6. A method for providing a reference frame for calculating recommended changes in sensor locations and clearly communicating the changes in a co-ordinate system that is clear to the user.
a. An example embodiment uses a set of reference AC coils (termed "beacons" as shown in FIGS. 1A, 1B and 4) which are fixed in space and operated under system control
i. In one example, the beacons are incorporated into a garment and sensed by the magnetometers, and the location of the magnetometers is then computed by the device
ii. In another example, the beacons are fixed in space around the patient 1. The location of the magnetometers relative to the beacons is computed
2. The location of the magnetometers relative to the maternal heart signal is computed
3. The fetal heart location is computed relative to the beacons and maternal heart iii. In one or both of the frameworks described in 6(a)(i) and 6(a)(ii), the beacons emit a known reference signal 1. The signal for each reference coil can be a sinusoid such that no two coils use the same frequency
2. The signals for each reference beacon may be controlled individually, such that the same frequency can be used sequentially for each coil
3. In one case, the AC reference signals can continue for the duration of the session
4. In another case, the AC reference signals can be turned off during heart signal measurement
5. In another case, the AC reference coils can emit a spread spectrum signal, with each coil broadcasting a unique identifier, a pseudo-random noise code, or PRN code, analogous to GPS signal generation
6. The signals for each reference beacon may be operated at the same frequency simultaneously a. In this case, they are treated as a single source that has a spatial distribution b. The spatial distribution is computed by the device c. The spatial distribution solution may be informed by measurements taken with the individual coils before operating them simultaneously iv. The embodiment contains one beacon or a plurality of beacons (e.g., as shown in FIGS. 1A, 1B and 4)

1. For unambiguous 3D localization of fetal heart signal, at least 4 reference beacons are required, which must not all be in the same geometric plane
2. In one example deployment, five beacons are used; two on each side and a fifth out of plane mounted at base of sternum or belly button v. In some embodiments, the beacons are not used because the reference frame can be established using other techniques b. Reference data may be fused with data from other imaging modalities or sensors i. In an example embodiment, the data is fused with ultrasonic images of the fetus 1. A reference beacon or plurality of beacons is fixed to the ultrasonic probe. The locations of these beacons are estimated to the ultrasonic imaging co-ordinates to the sensor co-ordinates
2. The ultrasonic and magnetic sensor data may be fused and displayed to the user for devices embodied with a display 7. A method for measuring and tracking fetal position and orientation using the described system and device embodiments. Herein, the method:

a. Tracks fetal heart position i. In one example, the heart's magnetic signature is approximated as a dipole source and estimates its strength, and location relative to the magnetometers and any beacons (e.g., 6 unknowns for fetal heart position, orientation and strength, or 5 unknowns if magnetic strength is estimated in another way).

ii. In another example, the fetal heart's magnetic signal is assumed to be a spatial distribution b. Estimates the physical geometry of the womb. The estimate may be generated by sensor data from magnetic sensors placed around the mother's abdomen i. The location of the sensors is used to estimate the surface contour of the abdomen ii. Sensors or beacons located at positions known to be at locations not on the abdominal surface may be or may not be used to further constrain the location of the womb c. Uses the estimation of the womb geometry to constrain the location of the fetal heart 8. A method where flux concentration enhances the signals measured by the magnetometers a. In an example, the flux concentration technique is implemented using a magnetic flux concentration coil, which may include a relatively large air-core coil and resonant capacitor b. In an example, incorporate high permeability materials of specific geometries or metamaterials with specific geometric structures In this patent document, the described technical solutions are configured to monitor the maternal and/or fetal heart rate. In some examples, monitoring the heart rate includes continually (or near continually) collecting data points associated with the maternal heart rate and/or fetal heart rate. In some examples, monitoring the heart rate includes tracking the heart rate, which may include both continually (or near continually) collecting data points associated with the heart rate and using a tracking loop, e.g., separate tracking loops to track the maternal heart rate and the fetal heart rate.

Figure 11:
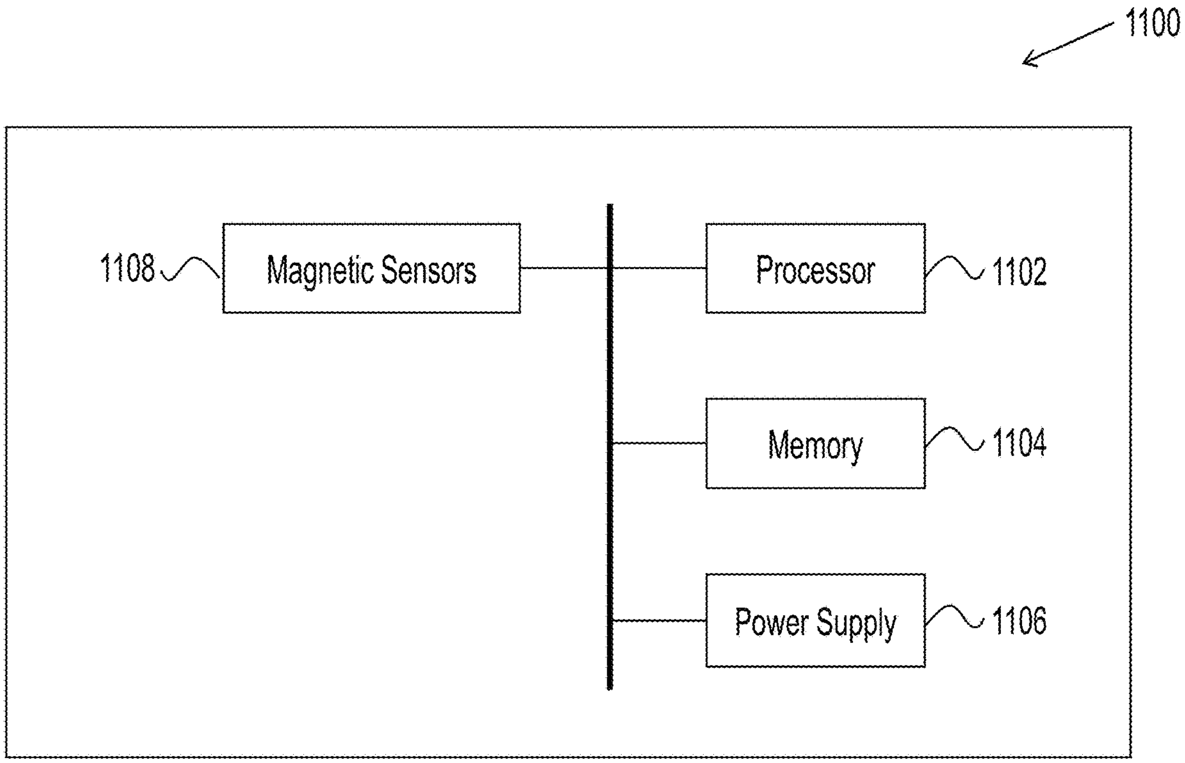
FIG. 11 is a block diagram illustrating an example system configured to implement embodiments of the disclosed technology.

FIG. 11 shows an example of a hardware platform 1100 that can be used to implement some of the techniques described in the present document. For example, the hardware platform 1100 may implement method 1000, or may implement the various modules and algorithms described herein. The hardware platform 1100 may include a processor 1102 that can execute code to implement a method. The hardware platform 1100 may include a memory 1104 that may be used to store processor-executable code and/or store data. The hardware platform 1100 may further include a power supply 1106 and magnetic sensors 1108, which can communicate with the processor 1102 using leads or a wireless protocol. The processor 1102 may be configured to implement de-noising and/or source separation algorithms. In some embodiments, the memory 1104 may comprise multiple memories, some of which are exclusively used by the processor 1102 when implementing the de-noising and source separation algorithms.

The following solutions for fetal magnetocardiography, which may be combined with the aspects enumerated above, may be preferably implemented by some embodiments.

1. A system for monitoring a fetal heart signal in a subject, comprising at least one magnetic sensor configured to measure a combined heart signal comprising a mixture of a maternal heart signal and the fetal heart signal, wherein the at least one magnetic sensor is configured to operate within a dynamic range from 0.01 pT to 1 mT and with a noise floor within a range from 0.01 pT/$\sqrt{\text{Hz}}$ to 100 pT/$\sqrt{\text{Hz}}$; and a processor configured to receive, from the at least one magnetic sensor, the combined heart signal, estimate, based on the combined heart signal, one or more parameters associated with a location or a motion of the at least one magnetic sensor, generate a de-noised combined heart signal by performing a de-noising operation on the combined heart signal, wherein the de-noising operation comprises a filtering operation configured based on the one or more parameters, and track, based on the de-noised combined heart signal, an estimate of the fetal heart signal.

2. The system of solution 1, wherein the filtering operation comprises a bandpass filtering operation and a notch filtering operation, and wherein the de-noising operation uses at least one of a bandpass filter for the bandpass filtering operation and a notched filter for the notch filtering operation, or a wavelet transform to implement the bandpass filtering operation and the notch filtering operation, or a neural network to implement the bandpass filtering operation and the notch filtering operation.
3. The system of any of the preceding solutions, wherein the at least one magnetic sensor is configured to operate in a magnetically unshielded environment and does not require cryogenic cooling.
4. The system of any of the preceding solutions, wherein the at least one magnetic sensor comprises a frequency response in a range from 0.1 Hz to 200 Hz.
5. The system of any of the preceding solutions, wherein the at least one magnetic sensor comprises a single-axis magnetometer or a three-axis magnetometer.
6. The system of any of the preceding solutions, wherein the processor is configured, as part of tracking the estimate of the fetal heart signal, to perform a source separation operation on the de-noised combined heart signal to generate an estimate of the maternal heart signal and the estimate of the fetal heart signal.
7. The system of solution 6, wherein the source separation operation uses at least one of an independent component analysis (ICA), or a principal component analysis (PCA), or a neural network, or wavelet analysis, to generate the estimate of the maternal heart signal from the combined heart signal.
8. The system of any of the preceding solutions, wherein the processor is configured, as part of tracking the estimate of the fetal heart signal, to seed at least one tracking loop with an estimate of the maternal heart signal to track the maternal heart signal and the fetal heart signal.
9. The system of solution 8, wherein the at least one tracking loop comprises a first tracking loop that tracks the maternal heart signal and a second tracking loop that operates in parallel with the first tracking loop and tracks the fetal heart signal.
10. The system of solution 9, wherein a Kalman filter is used to update parameters of the first tracking loop or the second tracking loop.
11. The system of any of the preceding solutions, comprising an inertial measurement unit, wherein the processor is configured to estimate the one or more parameters based additionally on an output of the inertial measurement unit.
12. The system of any of the preceding solutions, wherein each of the at least one magnetic sensor is positioned at an initial location on the subject.
13. The system of solution 12, comprising a handheld device, wherein the initial location of the at least one magnetic sensor on the subject is displayed on a display of the handheld device, wherein the processor is configured to measure a signal quality from the at least one magnetic sensor, determine, based on the signal quality, an adjustment to the initial location that improves the signal quality, and generating the location of the at least one magnetic sensor by applying the adjustment to the initial location of the at least one magnetic sensor, and wherein the location of the at least one magnetic sensor or the adjustment is displayed on the display of the handheld device.
14. The system of any of the preceding solutions, wherein the processor is configured to estimate the one or more parameters associated with the location or the motion of the at least one magnetic sensor based additionally on a reference frame.
15. The system of solution 14, wherein the reference frame is determined based on an estimate of the maternal heart signal.
16. The system of solution 14, comprising a plurality of beacons located on the subject, wherein the reference frame is determined based on one or more signals received from the plurality of beacons.
17. The system of solution 16, wherein each of the plurality of beacons is an alternating current magnetic coil configured to emit a corresponding signal.
18. The system of solution 17, wherein the one or more signals includes a spread-spectrum signal.
19. A method for monitoring a fetal heart signal in a subject, comprising receiving, from at least one magnetic sensor, a combined heart signal comprising a mixture of a maternal heart signal and the fetal heart signal, wherein the at least one magnetic sensor is configured to operate within a dynamic range from 0.01 pT to 1 mT and with a noise floor within a range from 0.01 pT/$\sqrt{\text{Hz}}$ to 100 pT/$\sqrt{\text{Hz}}$; estimating, based on the combined heart signal, one or more parameters associated with a location or a motion of the at least one magnetic sensor; generating a de-noised combined heart signal by performing a de-noising operation on the combined heart signal, wherein the de-noising operation comprises a filtering operation configured based on the one or more parameters; and tracking, based on the de-noised combined heart signal, an estimate of the fetal heart signal.
20. The method of any of the preceding solutions, wherein the filtering operation comprises a bandpass filtering operation and a notch filtering operation, and wherein the de-noising operation uses at least one of a bandpass filter, a wavelet transform, or a neural network.
21. The method of any of the preceding solutions, wherein the at least one magnetic sensor is configured to operate in a magnetically unshielded environment and does not require cryogenic cooling.
22. The method of any of the preceding solutions, wherein the at least one magnetic sensor comprises a frequency response in a range from 0.1 Hz to 200 Hz.
23. The method of any of the preceding solutions, wherein the at least one magnetic sensor comprises a single-axis magnetometer or a three-axis magnetometer.
24. The method of any of the preceding solutions, wherein tracking the estimate of the fetal heart signal comprises performing a source separation operation on the de-noised combined heart signal to generate an estimate of the maternal heart signal and the estimate of the fetal heart signal.
25. The method of solution 24, wherein the estimate of the maternal heart signal is generated based on the source separation operation that uses at least one of an independent component analysis (ICA), a principal component analysis (PCA), a neural network, or wavelet analysis.

26. The method of any of the preceding solutions, wherein tracking the estimate of the fetal heart signal comprises seeding at least one tracking loop with the estimate of the maternal heart signal to track the maternal heart signal and the fetal heart signal.
27. The method of solution 26, wherein the at least one tracking loop comprises a first tracking loop that tracks the maternal heart signal and a second tracking loop that operates in parallel with the first tracking loop and tracks the fetal heart signal.
28. The method of solution 27, wherein a Kalman filter is used to update parameters of the first tracking loop or the second tracking loop.
29. The method of any of the preceding solutions, wherein estimating the one or more parameters associated with the location or the motion of the at least one magnetic sensor is further based on using an inertial measurement unit.
30. The method of any of the preceding solutions, further comprising measuring a signal quality from the at least one magnetic sensor; determining, based on the signal quality, an adjustment to an initial location that maximizes the signal quality; and generating the location of the at least one magnetic sensor by applying the adjustment to the initial location of the at least one magnetic sensor.
31. The method of solution 30, wherein the location of the at least one magnetic sensor or the adjustment is displayed on a display of a handheld device.
32. The method of any of the preceding solutions, wherein estimating the one or more parameters is based additionally on a reference frame.
33. The method of solution 32, wherein the reference frame is determined based on the estimate of the maternal heart signal.
34. The method of solution 32, wherein the reference frame is determined based on a signal received from each of a plurality of beacons.
35. The method of solution 34, wherein each of the plurality of beacons is an alternating current magnetic coil configured to emit the signal.
36. The method of solution 35, wherein the signal is a spread-spectrum signal.
37. A method for implementing de-noising and source separation algorithms to separate fetal heat rate signal and a maternal heart rate signal from at least one signal measured by one or more magnetometers on a subject, and determining fetal position and orientation.
38. The method of solution 37, further comprising providing feedback on locations of the one or more magnetometers.
39. The method of solution 37 or 38, wherein a reference frame is provided for implementing the de-noising and source separation algorithms and optimizing locations of the one or more magnetometers on the subject.
40. The method of solution 39, wherein the reference frame is based on a plurality of beacons.
41. The method of solution 39, wherein the reference frame is based on the maternal heart rate signal.
42. An apparatus comprising at least one processor that is configured to implement the method in one or more of solutions 19 to 41.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and devices can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, these are optional. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements, and variations can be made based on what is described and illustrated herein.

What is claimed is:

1. A system for monitoring a fetal heart signal in a subject, comprising:

at least one magnetic sensor configured to measure a combined heart signal comprising a mixture of a maternal heart signal and the fetal heart signal, wherein the at least one magnetic sensor is configured to operate within a dynamic range from 0.01 pT to 1 mT and with a noise floor within a range from 0.01 $pT/\sqrt{Hz}$ to 100 $pT/\sqrt{Hz}$; and a processor configured to:

receive, from the at least one magnetic sensor, the combined heart signal, estimate, based on the combined heart signal, one or more parameters associated with a location or a motion of the at least one magnetic sensor, generate a de-noised combined heart signal by performing a de-noising operation on the combined heart signal, wherein the de-noising operation comprises an adaptive filtering operation, and wherein the one or more parameters are input to the adaptive filtering operation, and track, based on the de-noised combined heart signal, an estimate of the fetal heart signal.

2. The system of claim 1, wherein the adaptive filtering operation comprises a bandpass filtering operation and a notch filtering operation, and wherein the de-noising operation uses at least one of:

a bandpass filter for the bandpass filtering operation and a notched filter for the notch filtering operation, or a wavelet transform to implement the bandpass filtering operation and the notch filtering operation, or a neural network to implement the bandpass filtering operation and the notch filtering operation.

3. The system of claim 1, wherein the at least one magnetic sensor is configured to operate in a magnetically unshielded environment and does not require cryogenic cooling.

4. The system of claim 1, wherein the at least one magnetic sensor comprises a frequency response in a range from 0.1 Hz to 200 Hz.

5. The system of claim 1, wherein the at least one magnetic sensor comprises a single-axis magnetometer or a three-axis magnetometer.

6. The system of claim 1, comprising:

an inertial measurement unit, wherein the one or more parameters are represented using a quaternion algebra or a combination of Cartesian co-ordinates and Euler angles, and wherein the processor is configured to estimate the one or more parameters based additionally on an output of the inertial measurement unit.

7. The system of claim 1, wherein each of the at least one magnetic sensor is positioned at an initial location on the subject.

8. The system of claim 7, comprising:

a handheld device, wherein the initial location of the at least one magnetic sensor on the subject is displayed on a display of the handheld device, wherein the processor is configured to:

measure a signal quality from the at least one magnetic sensor, determine, based on the signal quality, an adjustment to the initial location that improves the signal quality, and generate the location of the at least one magnetic sensor by applying the adjustment to the initial location of the at least one magnetic sensor, and wherein the location of the at least one magnetic sensor or the adjustment is displayed on the display of the handheld device.

9. The system of claim 1, wherein the processor is configured to estimate the one or more parameters associated with the location or the motion of the at least one magnetic sensor based additionally on a reference frame, and wherein the one or more parameters are represented using a quaternion algebra or a combination of Cartesian co-ordinates and Euler angles.

10. The system of claim 9, wherein the reference frame is determined based on an estimate of the maternal heart signal.

11. The system of claim 9, comprising:

a plurality of beacons located on the subject, wherein the reference frame is determined based on one or more signals received from the plurality of beacons.

12. The system of claim 11, wherein each of the plurality of beacons is an alternating current magnetic coil configured to emit a corresponding signal.

13. The system of claim 12, wherein the one or more signals includes a spread-spectrum signal.

14. A method for monitoring a fetal heart signal in a subject, comprising:

receiving, from at least one magnetic sensor, a combined heart signal comprising a mixture of a maternal heart signal and the fetal heart signal, wherein the at least one magnetic sensor is configured to operate within a dynamic range from 0.01 pT to 1 mT and with a noise floor within a range from 0.01 $pT/\sqrt{Hz}$ to 100 $pT/\sqrt{Hz}$;

estimating, based on the combined heart signal, one or more parameters associated with a location or a motion of the at least one magnetic sensor;

generating a de-noised combined heart signal by performing a de-noising operation on the combined heart signal, wherein the de-noising operation comprises an adaptive filtering operation, and wherein the one or more parameters are input to the adaptive filtering operation; and tracking, based on the de-noised combined heart signal, an estimate of the fetal heart signal.

15. The method of claim 14, wherein tracking the estimate of the fetal heart signal comprises:

performing a source separation operation on the de-noised combined heart signal to generate an estimate of the maternal heart signal and the estimate of the fetal heart signal.

16. The method of claim 15, wherein the estimate of the maternal heart signal is generated based on the source separation operation that uses at least one of an independent component analysis (ICA), a principal component analysis (PCA), a neural network, or wavelet analysis.

17. The method of claim 14, wherein tracking the estimate of the fetal heart signal comprises:

seeding at least one tracking loop with the estimate of the maternal heart signal to track the maternal heart signal and the fetal heart signal.

18. The method of claim 17, wherein the at least one tracking loop comprises a first tracking loop that tracks the maternal heart signal and a second tracking loop that operates in parallel with the first tracking loop and tracks the fetal heart signal.

19. The method of claim 18, wherein a Kalman filter is used to update parameters of the first tracking loop or the second tracking loop, and wherein the parameters comprise a frequency or a phase of a corresponding heart signal.

20. The method of claim 14, further comprising:

measuring a signal quality from the at least one magnetic sensor;

determining, based on the signal quality, an adjustment to an initial location that maximizes the signal quality; and generating the location of the at least one magnetic sensor by applying the adjustment to the initial location of the at least one magnetic sensor.

21. The method of claim 14, wherein an operation of the at least one magnetic sensor is based on tunneling magnetoresistance, giant spin resonance, magneto-impedance, or fluxgate magnetometry, and wherein the at least one magnetic sensor is configured to operate in a magnetically unshielded environment and does not require cryogenic cooling.

* * * * *